(12) United States Patent
Kawasaki et al.

(10) Patent No.: US 8,888,682 B2
(45) Date of Patent: Nov. 18, 2014

(54) WIRELESS IMAGE ACQUISITION SYSTEM

(75) Inventors: Shinya Kawasaki, Sagamihara (JP); Koichi Niida, Hachoiji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1132 days.

(21) Appl. No.: 12/411,779

(22) Filed: Mar. 26, 2009

(65) Prior Publication Data
US 2009/0247824 A1 Oct. 1, 2009

(30) Foreign Application Priority Data
Mar. 27, 2008 (JP) ................................. 2008-084533

(51) Int. Cl.
- *A61B 1/04* (2006.01)
- *A61B 1/00* (2006.01)
- *H04N 7/18* (2006.01)
- *A61B 5/00* (2006.01)

(52) U.S. Cl.
CPC .............. *H04N 7/18* (2013.01); *A61B 1/00055* (2013.01); *A61B 1/00016* (2013.01); *A61B 1/00009* (2013.01); *A61B 1/042* (2013.01); *A61B 5/0084* (2013.01)
USPC ........................ 600/109; 600/160; 235/462.01

(58) Field of Classification Search
CPC ................................................. G06K 7/10584
USPC .......................... 600/103, 109, 117–118, 160; 235/462.01, 462.45, 462.46
See application file for complete search history.

(56) References Cited

U.S. PATENT DOCUMENTS

| | | | | |
|---|---|---|---|---|
| 4,633,304 | A | * 12/1986 | Nagasaki | 348/69 |
| 5,609,560 | A | * 3/1997 | Ichikawa et al. | 600/101 |
| 6,141,037 | A | * 10/2000 | Upton et al. | 348/65 |
| 6,311,540 | B1 | * 11/2001 | Paltieli et al. | 73/1.82 |

(Continued)

FOREIGN PATENT DOCUMENTS

| | | |
|---|---|---|
| JP | 60-48011 A | 3/1985 |
| JP | 2001-184452 A | 7/2001 |

(Continued)

OTHER PUBLICATIONS

European Search Report dated Jun. 10, 2009, issued in corresponding European Patent Application No. 090004398.5.

(Continued)

*Primary Examiner* — John P Leubecker
*Assistant Examiner* — Arnaldo Torres Diaz
(74) *Attorney, Agent, or Firm* — Westerman, Hattori, Daniels & Adrian, LLP

(57) ABSTRACT

A wireless image acquisition system includes an image acquisition apparatus configured to transmit acquired image information by radio waves, and an image receiving unit configured to receive and display the image information transmitted from the image acquisition apparatus. A display unit of the image receiving unit displays wireless communication setting information. An image acquisition unit of the image acquisition apparatus captures the wireless communication setting information, and a communication setting unit makes wireless communication setting of the image acquisition apparatus based on the captured wireless communication setting information. One of the image acquisition apparatus and image receiving unit further includes a detection unit configured to detect that the distance from the image acquisition unit to the display unit is within a predetermined value when the wireless communication setting information is captured, and a warning unit configured to give a warning when the detected distance is within the predetermined value.

10 Claims, 6 Drawing Sheets

(56) References Cited

U.S. PATENT DOCUMENTS

| | | | |
|---|---|---|---|
| 6,557,764 B1* | 5/2003 | Reasoner et al. | 235/455 |
| 6,902,529 B2* | 6/2005 | Onishi et al. | 600/118 |
| 6,950,025 B1* | 9/2005 | Nguyen | 340/573.1 |
| 7,193,219 B2* | 3/2007 | Schick et al. | 250/370.11 |
| 7,596,359 B2* | 9/2009 | Kimoto et al. | 455/137 |
| 2002/0082474 A1* | 6/2002 | Yamamoto | 600/111 |
| 2006/0208088 A1 | 9/2006 | Sekiguchi | |
| 2006/0217591 A1 | 9/2006 | Abe | |
| 2007/0078484 A1* | 4/2007 | Talarico et al. | 606/205 |
| 2008/0144726 A1* | 6/2008 | Ingber et al. | 375/240.28 |

FOREIGN PATENT DOCUMENTS

| | | |
|---|---|---|
| JP | 2001-353124 A | 12/2001 |
| JP | 2004-266628 A | 9/2004 |
| JP | 2006-135930 A | 5/2006 |
| JP | 2006-244139 A | 9/2006 |
| JP | 2006-261938 A | 9/2006 |
| JP | 2006-271432 A | 10/2006 |
| JP | 2006-271433 A | 10/2006 |
| WO | 2007/070831 A2 | 6/2007 |

OTHER PUBLICATIONS

Jpanaese Office Action dated Jul. 17, 2012, issued in corresponding Japanese Office Action 2008-084533, (6 pages). With English Translation.

* cited by examiner

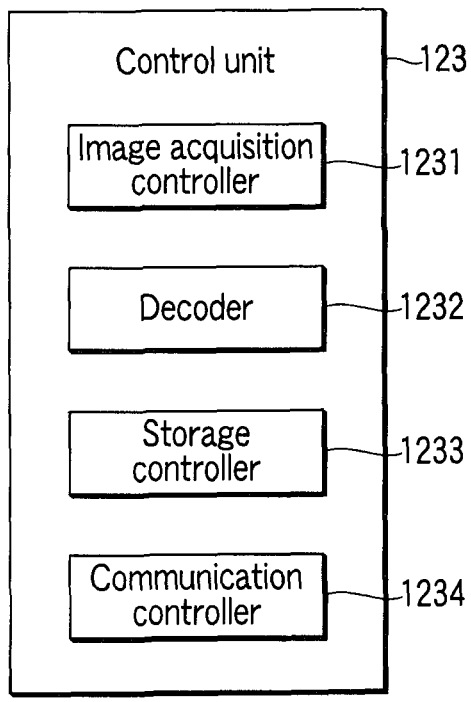
FIG. 2
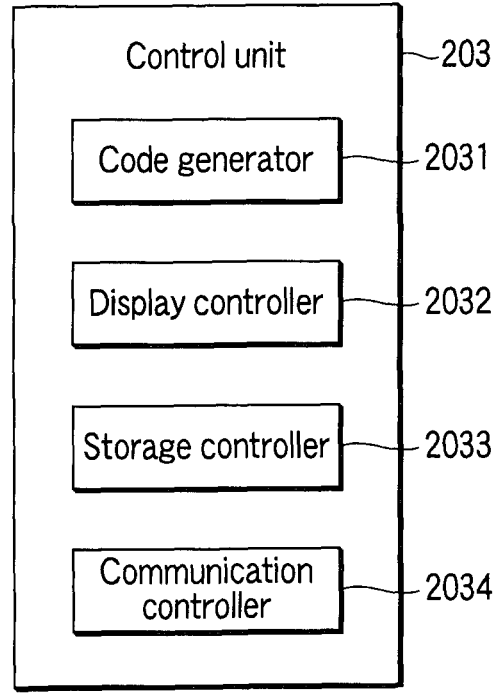
FIG. 3
| SSID | ABCD_UNIT_**** |
|---|---|
| CH | 2 |
| WEP | OFF |
| MODE | 2.4G |
FIG. 4

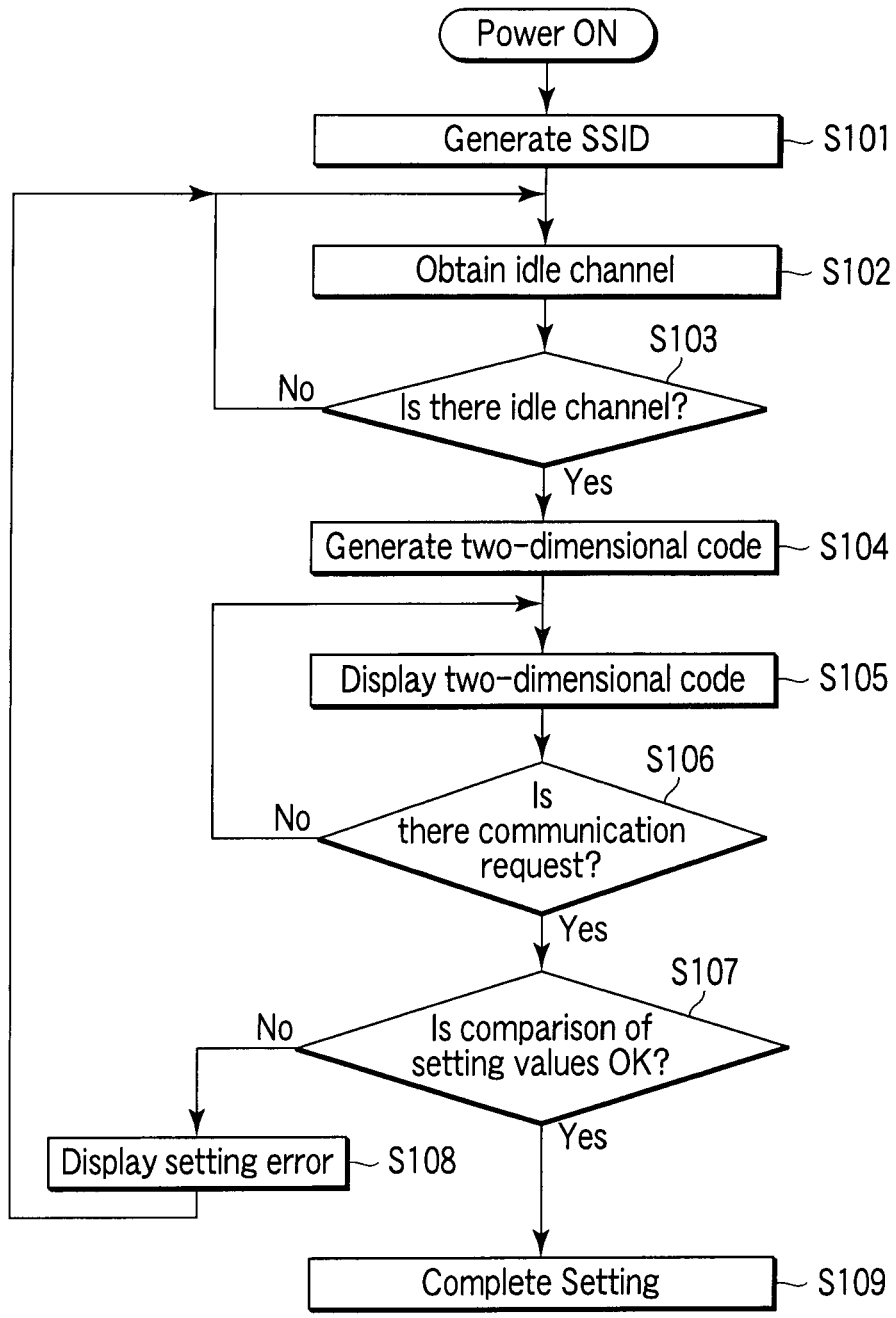
F I G. 5

WIRELESS IMAGE ACQUISITION SYSTEM

CROSS-REFERENCE TO RELATED APPLICATIONS

This application is based upon and claims the benefit of priority from prior Japanese Patent Application No. 2008-084533, filed Mar. 27, 2008, the entire contents of which are incorporated herein by reference.

BACKGROUND OF THE INVENTION

1. Field of the Invention

The present invention relates to a wireless image acquisition system, which transmits acquired image information to an image receiving unit by radio waves.

2. Description of the Related Art

In recent years, there has been widely used an endoscope system which can observe an image of a subject in an abdominal cavity or path by inserting a slender insertion tube part into an abdominal cavity or path.

Such an endoscope system generally comprises an endoscope assembly, a light source unit, a light guide cable, an image acquisition unit, a video processor, a signal cable, and a monitor unit. The endoscope assembly has an insertion tube part, which is inserted into an abdominal cavity or path. The light source unit is provided separately from the endoscope assembly, and supplies an illumination light to the endoscope assembly. The light guide cable leads the illumination light from the light source unit to the endoscope assembly. The image acquisition unit is built in or removably provided in the endoscope assembly, and captures a subject and obtains its image data. The video processor is provided separately from the endoscope assembly, and converts the image data obtained by the endoscope assembly into a video signal displayable on a monitor. The signal cable is used to transmit the image data from the endoscope assembly to the video processor. The monitor unit displays the video signal obtained by the video processor. Therefore, the endoscope assembly is connected to the light source unit and video processor, which are external units, through the light guide cable and the signal cable. This limits a movable range of the endoscope assembly, and disturbs the operability of the endoscope assembly.

Under the circumstances, U.S. Pat. No. 4,633,304 discloses the following endoscope system. In this endoscope system, an illumination unit comprising a light-emitting diode (LED) is incorporated in an endoscope assembly. Thereby, a light guide cable extended from an endoscope assembly is eliminated. The endoscope assembly is provided with a video signal processing circuit, which obtains a video signal displayable on a monitor by processing image data, and a transmission circuit, which transmits the video signal by radio waves. A data processing unit, which receives the radio waves from the transmission circuit, and demodulates the video signal, is provided separately from the endoscope assembly. Thereby, a signal cable extended from the endoscope assembly is eliminated. Such an endoscope system is generally called a wireless endoscope system, and has advantages that a movable range of the endoscope assembly is not limited, and the operability of the endoscope assembly is improved.

As another example of a wireless endoscope system, Jpn. Pat. Appln. KOKAI Publication No. 2004-266628 proposes a wireless endoscope system, in which a radio frequency used for an external transmission signal is detected by a receiver, and whether the received frequency band is usable or not is determined. Further, Jpn. Pat. Appln. KOKAI Publication Nos. 2006-271432 and 2006-271433 propose a wireless endoscope system, in which a usable idle channel is detected, and a channel is automatically set according to the detection result. However, in the above patent applications Nos. 2004-266628, 2006-271432 and 2006-271433, setting of a radio channel is considered, but a method of safe secure connection and setting including other parameters such as SSID is not considered.

To solve the above problem, Jpn. Pat. Appln. KOKAI Publication No. 2006-261938 discloses a method of storing SSID and encryption parameter necessary for setting communication as two-dimensional codes, displaying the two-dimensional codes in a display unit, and reading the displayed two-dimensional codes by a code reader, thereby acquiring communication setting parameters.

BRIEF SUMMARY OF THE INVENTION

According to one aspect of the invention, there is provided a wireless image acquisition system including an image acquisition apparatus configured to transmit acquired image information by radio waves, and an image receiving unit configured to receive and display the image information transmitted from the image acquisition apparatus, comprising:

a display unit which is provided in the image receiving unit, and is configured to display wireless communication setting information required by the image acquisition apparatus for making communication with the image receiving unit;

an image acquisition unit which is provided in the image acquisition apparatus, and is configured to capture the wireless communication setting information displayed on the display unit;

a communication setting unit which is provided in the image acquisition apparatus, and is configured to make wireless communication setting of the image acquisition apparatus, based on the wireless communication setting information captured by the image acquisition unit;

a detection unit which is provided in one of the image acquisition apparatus and image receiving unit, and is configured to detect that the distance from the image acquisition unit to the display unit is within a predetermined value when the wireless communication setting information is captured; and a warning unit which is provided in one of the image acquisition apparatus and image receiving unit, and is configured to give a warning when the detection unit detects that the distance from the image acquisition unit to the display unit is within the predetermined value.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing a configuration of a control unit of an endoscope assembly;

FIG. 3 is a diagram showing a configuration of a control unit of an image receiving unit;

FIG. 4 is a diagram showing an example of parameters to be stored in a two-dimensional code;

FIG. 5 is a flowchart for explaining a setting operation in an image receiving unit;

DETAILED DESCRIPTION OF THE INVENTION

Hereinafter, a best mode for embodying the invention will be explained with reference to the accompanying drawings.

Figure 1:
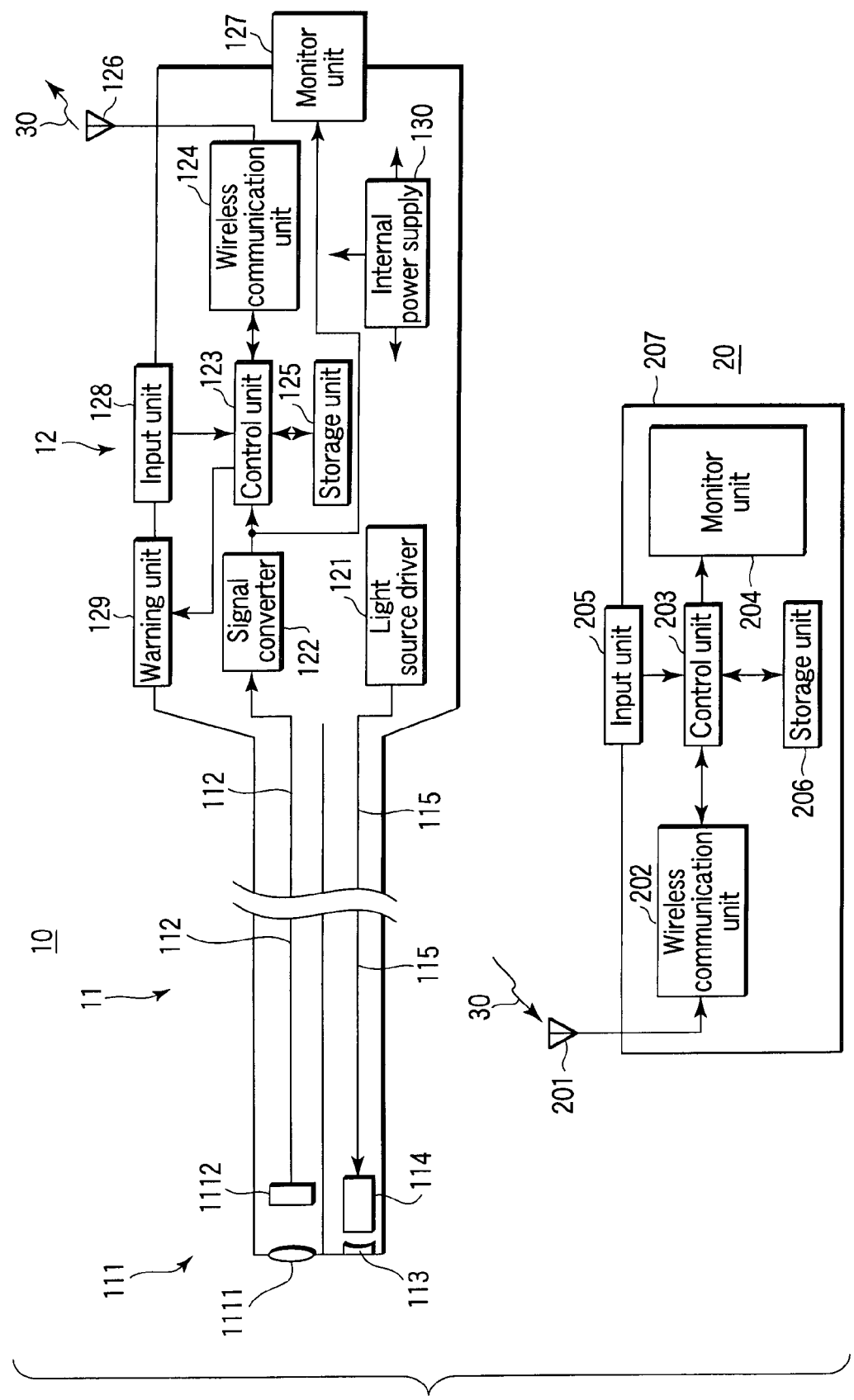
FIG. 1 is a block diagram showing a configuration of a wireless image acquisition system according to a first embodiment of the invention.

As shown in FIG. 1, a wireless image acquisition system according to a first embodiment of the invention includes an endoscope assembly 10, and an image receiving unit 20. The endoscope assembly 10 is an image acquisition apparatus for transmitting acquired image information by radio waves. The image receiving unit 20 receives and displays the image information transmitted from the endoscope assembly 10. In FIG. 1, the endoscope assembly 10 and image receiving unit 20 are shown only one each, but two or more can be used.

The endoscope assembly 10 comprises an insertion part 11 to be inserted into a patient body cavity or path, and an operation unit 12 connected to the insertion part 11.

The insertion part 11 is made of metallic material or flexible member. The inside of the insertion part 11 is divided into two parts, one is the image acquisition side, and the other is the light source side. The image acquisition side of the insertion part 11 is provided with an image acquisition unit 111 at the distal end. The image acquisition unit 111 comprises a camera lens 1111, and an image sensor 1112. The image sensor 1112 is a CCD, for example, which receives a optical image entered through the camera lens 1111, and converts it into an electric signal as image information. The electric signal from the image sensor 1112 is sent to an electric circuit of the operation unit 12 through a signal lead wire 112. The light source side of the insertion part 11 is provided with an illumination lens 113 at the distal end. A light source unit 114 is arranged in the rear of the illumination lens 113, and light from the light source unit 114 is applied to an observing part through the illumination lens 113. The light source unit 114 is composed of an LED or a lamp, and is connected to a light source driver 121 in the operation unit 12 through a lead wire 115.

The operation unit 12 contains a signal converter 122, a control unit 123, a wireless communication unit 124, and a storage unit 125, in addition to the light source driver 121. The electric signal from the above image sensor 1112 is converted to a video signal by the signal converter 122. The video signal is sent to the wireless communication unit 124 through the control unit 123, and transmitted as a radio wave 30 from an antenna 126. The signal converter 122 is connected to a compact monitor unit 127 such as a liquid crystal monitor. The control unit 123 is connected to an input unit 128 and a warning unit 129. The input unit 128 is provided with switches, such as a power switch to instruct ON/OFF of power supply, and a freeze save switch to instruct saving of an observing image. The warning unit 129 includes an LED and a buzzer, for example. The storage unit 125 is a register to store communication setting information to be described later, and various information including image acquisition control information and additional information.

The light source driver 121, signal converter 122, control unit 123, wireless communication unit 124, monitor unit 127, and warning unit 129 are connected to an internal power supply 130 such as a battery, and are driven with the power supply 130.

The monitor unit 127 can be eliminated. It is possible to use an external power supply for driving the components, instead of the internal power supply 130. It is also possible to guide an illumination light from an external light source to the distal end of the insertion part 11, by providing a light guide as in a conventional endoscope assembly, instead of the light source unit 114, lead wire 115 and light source driver 121 in FIG. 1. The light source unit can be provided in the operation unit 12, and a light guide can be provided to guide an illumination light to the distal end of the insertion part 11.

In the endoscope assembly 10 configured as described above, when the insertion part 11 is inserted into a patient's body cavity or path, and the light source unit 114 emits light to an observing part, the image sensor 1112 receives the light from the observing part. The signal converter 122 converts an optical image received by the image sensor 1112 into an electric video signal (image information), and transfers it to the control unit 123. The control unit 123 sends the image information to the wireless communication unit 124, by adding information such as switch information needed to sent to the receiving side. The wireless communication unit 124 converts the received information into a high-frequency signal, and transmits it as a radio wave 30 from the antenna 126.

The radio wave 30 transmitted as described above is received by the image receiving unit 20. The image receiving unit 20 comprises an antenna 201, a wireless communication unit 202, a control unit 203, a monitor unit 204, an input unit 205, and a storage unit 206. The radio wave 30 received by the antenna 201 is sent to the wireless communication unit 202, in which the radio wave is demodulated to the original information. The demodulated information is sent to the control unit 203. The control unit 203 determines ON/OFF of the freeze saving switch according to the received information, and saves a freeze image to the storage unit 206, sends and displays an observing image to/in the monitor unit 204. The input unit 205 is a set of switches including a power supply switch. The storage unit 206 stores communication setting information, image acquisition control information, and additional information.

A monitor apparatus may be connected to the image receiving unit 20 for displaying an image, instead of providing the monitor unit 204 in the image receiving unit 20.

Radio waves are not necessarily be transmitted from the operation unit 12 of the endoscope assembly 10, and received by the image receiving unit 20. It is advantageous for reliability and expansion of functions to provide a function of transmitting radio waves from the image receiving unit 20 to the operation unit 12 for the purpose of confirming transmission and reception of data.

As shown in FIG. 2, the control unit 123 of the endoscope assembly 10 has an image acquisition controller 1231, a decoder 1232, a storage controller 1233, and a communication controller 1234. The image acquisition controller 1231 controls the image acquisition unit 111, which is not connected with a wire in the drawing. Specifically, the control includes brightness adjustment, and white balance adjustment. The decoder 1232 extracts communication setting information from an acquired image of a two-dimensional code. The storage controller 1233 stores the extracted communication setting information, image acquisition control information and additional information, in the storage unit 125. The communication controller 1234 receives communication data from the wireless communication unit 124, or sends communication data to the wireless communication unit 124.

As shown in FIG. 3, the control unit 203 of the image receiving unit 20 has a code generator 2031, a display controller 2032, a storage controller 2033, and a communication controller 2034. The code generator 2031 generates a two-dimensional code storing communication setting information. The display controller 2032 displays the generated two-dimensional code on the monitor unit 204. The storage controller 2033 stores communication setting information, image acquisition control information and additional information, in the storage unit 206. The communication controller 2034 receives communication data from the wireless communication unit 202, or sends communication data to the wireless communication unit 202.

The communication setting information stored in a two-dimensional code generated by the code generator 2031 includes channel setting, and a network ID. The communication controller 2034 obtains an already used channel from a radio wave received by the wireless communication unit 202 through the antenna 201, and identifies an unused channel. The communication controller 2034 sends the information about the identified channel to the storage controller 2033 as channel setting. The storage controller 2033 stores the information in the storage unit 206. The code generator 2031 reads communication setting information including the above channel information stored in the storage unit 206, and stores the information in a two-dimensional code.

In this embodiment, a SSID used in a wireless LAN, for example, is used as a network ID that is a recognition code of the image receiving unit 20. The endoscope assembly 10 is designed to be able to communicate with a specific unit only, such as an image receiving unit 20, and a part of the SSID is fixed (e.g. SSID=[ABCD_UNIT_****], the "*" part is a serial number given for each image receiving unit 20). A SSID may be generated by generating a random number. An example of communication setting information is shown in FIG. 4. The example in the drawing shows a case including encryption and communication mode. WEP is used as encryption. In the example shown in the drawing, WEP is OFF, but it may be ON. Encryption other than WEP is of course permitted (e.g. TKIP and AES). A communication mode (MODE) is set to use a 2.4 GHz band. But, another band, for example, 5 GHz may be used. WEP and MODE can be optionally set by the user.

Next, an explanation will be given of the operation of the wireless image acquisition system configured as described above, by referring to FIGS. 5 and 6.

As shown in FIG. 5, when the power supply of the image receiving unit 20 is turned on, the control unit 203 obtains a SSID from the storage unit 206 by the storage controller 2033, or generates a SSID by generating a random number (step S101) FIG. 5. The communication controller 2034 obtains an already used channel by using the wireless communication unit 202, thereby obtaining a usable channel, or an idle channel (step S102). Whether an idle channel exists or not is determined (step S103). When an idle channel does not exist, step S102 is resumed. Namely, an idle channel is waited.

Figure 7:
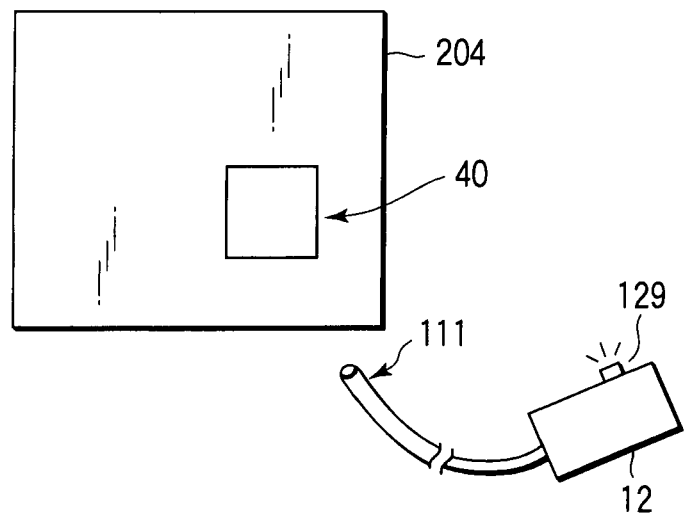
FIG. 7 is a diagram showing a relationship between an endoscope assembly and an image receiving unit, when a two-dimensional code is displayed.

When existence of an idle channel is determined in step S103, the code generator 2031 generates a two-dimensional code (step S104). The display controller 2032 displays the generated two-dimensional code in the monitor unit 204 (step S105). A position to display the two-dimensional code is optional, but desirably a position easy to be captured by the endoscope assembly 10. In this embodiment, as shown in FIG. 7, a two-dimensional code 40 is displayed in the lower right of the display screen of the monitor unit 204.

Thereafter, the communication controller 2034 checks whether a communication start request is received from the endoscope assembly 10, by the wireless communication unit 202, and determines whether a communication start request is received or not (step S106). When a communication start request is not received, step S105 is resumed. Namely, a communication start request is waited.

Figure 6:
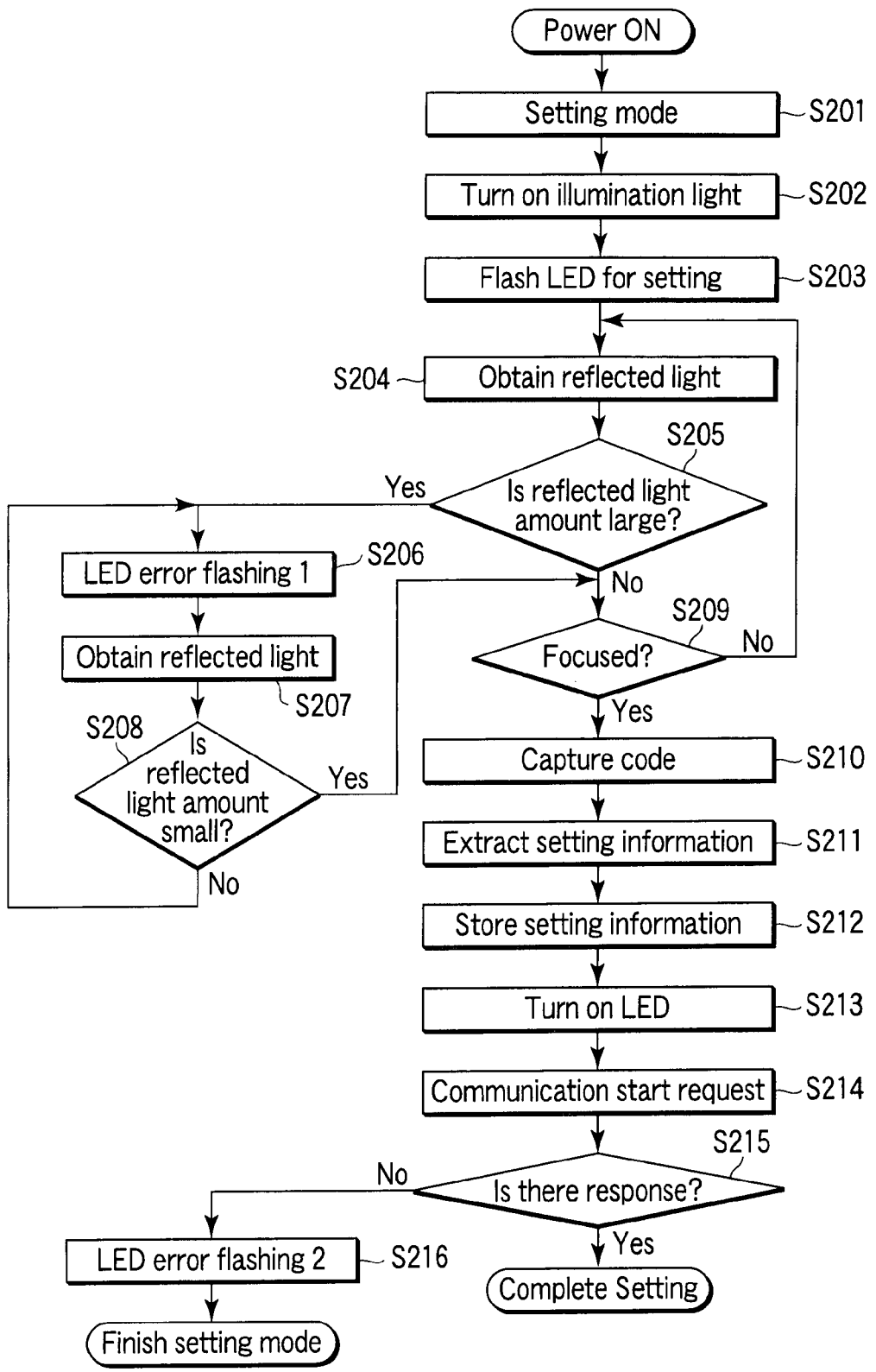
FIG. 6 is a flowchart for explaining a setting operation in an endoscope assembly.

As shown in FIG. 6, when the power supply of the endoscope assembly 10 is turned off, the control unit 123 checks the battery power, and goes to a setting mode FIG. 6 (step S201).

Figure 8:
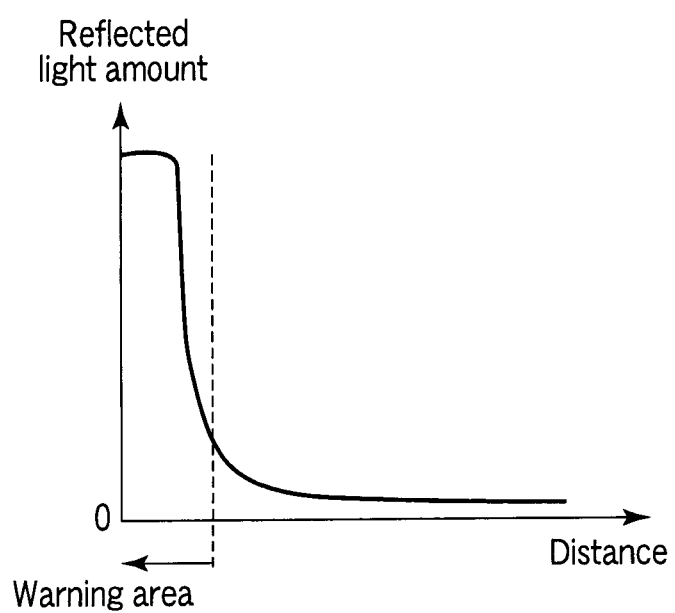
FIG. 8 is a graph showing a relationship between the amount of reflected light and distance.

In the setting mode, the image acquisition controller 1231 controls the light source driver 121, and turns on the light source 114 to emit light (step S202). The LED of the warning unit 129 flashes at predetermined intervals as a warning of communication setting (step S203). By bringing the image acquisition unit 111 close to the monitor unit 204 of the image receiving unit 20 in this setting mode, the two-dimensional code 40 displayed on the monitor unit 204 is captured. In this time, the light generated by driving the light source unit 114 is intermittently emitted through the illumination lens 113. The emitted light is reflected on the display screen surface of the monitor unit 204, and is partially applied to the image acquisition unit 111 as a reflected light. The image acquisition unit 111 obtains the amount of the reflected light by analog-to-digital conversion (step S204), and determines whether the amount is larger than a predetermined value (step S205). The reflected light amount varies depending on the distance from the image acquisition unit 111 to the display screen surface of the monitor unit 204 as shown in FIG. 8.

Therefore, when the reflected light amount is larger than a predetermined value, the distance is within a predetermined value, that is, the distance is too close. In such a case, the LED of the warning unit 129 flashes in a pattern indicating the extremely close distance, thereby warning the user that the distal end of the imaging pickup unit 111 is too close to the display screen surface of the monitor unit 204 (step S206). The distance may be determined by a relative amount of reflected light, based on a case in which the distance from the image acquisition unit 111 to the display screen surface of the monitor unit 204 is sufficiently separated, and there is no reflected light. The reflected light amount is obtained again in the image acquisition unit 111 by analog-to-digital conversion (step S207), and whether the reflected light amount is smaller than the predetermined value is determined (step S208). If the reflected light amount is not smaller than the predetermined value, step S206 is resumed, and a warning is continued.

When the reflected light amount is determined to be smaller than the predetermined value in step S205 or S208, whether focus is achieved is determined (step S209). Whether focus is achieved is determined by using a general contrast method. If focus is not achieved on the two-dimensional code 40 displayed on the monitor unit 204, step S204 is resumed.

In contrast, when focus is achieved on the two-dimensional code 40 displayed on the monitor unit 204, the image acquisition unit 111 captures the two-dimensional code 40 by controlling of the image acquisition controller 1231 (step S210). The decoder 1232 decodes the code from the acquired image information of the two-dimensional code 40, and extracts communication setting information (step S211). The storage unit 125 stores the extracted communication setting information by controlling of the storage controller 1233 (step S212). When the storing of the communication setting information is completed, the LED of the warning unit 129 is continuously lit, thereby notifying the user of the completion of setting (step S213). The completion of setting may be notified to the user by the LED of the warning unit 129, when communication setting information is extracted, a two-dimensional code is recognized, or focus is achieved, other than the timing when the storing of communication setting information is completed.

Thereafter, the wireless communication unit 124 transmits a communication start request by controlling of the communication controller 1234, based on the communication setting information stored in the storage unit 125 (step S214).

As shown in FIG. 5, in the image receiving unit 20, the control unit 203 determines whether the wireless communication unit 202 receives the communication start request by controlling of the communication controller 2034, in step S106. When reception of the communication start request is confirmed, the setting values of the received communication setting information and the communication setting information stored in the storage unit 206 are compared (step S107). The contents of the communication setting information generated by the image receiving unit 20 are the same as the contents of communication setting information decoded by the endoscope assembly 10 and transmitted by a communication start request. Therefore, if the result of the comparison is not the same, the display controller 2032 displays a setting error on the monitor unit 204 (step S108), and step S102 is resumed. When the result of the comparison is the same, the wireless communication unit 202 returns a response by controlling of the communication controller 2034, as a notice to indicate completion of communication setting (step S109).

As shown in FIG. 6, in the endoscope assembly 10, the control unit 123 determines whether the wireless communication unit 124 returns the response by the communication controller 1234 (step S215). If the response is not returned, the LED of the warning unit 129 flashes in a pattern to indicate a failure in starting communication (step S216), and the setting mode is finished. When the return of response is confirmed, communication is started. Namely, as described above, the contents of the communication setting information generated by the image receiving unit 20 are the same as the contents of communication setting information decoded by the endoscope assembly 10, and communication is possible between the image receiving unit 20 and endoscope assembly 10. When the communication setting is completed, the endoscope assembly 10 is shifted to an observation mode. Therefore, an image acquired by the image acquisition unit 111 of the endoscope assembly 10 is transmitted to the wireless communication unit 124 by the radio wave 30, received by the antenna 201 of the image receiving unit 20, and subjected to a predetermined image processing. The resultant image is displayed on the monitor unit 204.

It is also possible to display a message to state that the setting is completed or failed, in the monitor unit 204 of the image receiving unit 20, when the communication setting is competed or failed.

As described above, according to the first embodiment, the image acquisition unit 111 of the endoscope assembly 10 can be brought unnecessarily close to the monitor unit 204, and they are prevented from contacting. Therefore, even if two or more same type endoscope assembly 10 are provided in adjacent places, a user can cleanly, securely and easily start communication between the endoscope assembly 10 at hand and the image receiving unit 20 right before.

Besides, there is no possibility that the insertion part 11 that is a part to be inserted into a patient contacts the monitor unit 204 that is an unclean part, and the insertion part 11 can be kept clean. This is particularly effective for the endoscope assembly 10.

Further, as the endoscope assembly 10 detects that the distance from the image acquisition unit 111 to the monitor unit 204 of the image receiving unit 20 is within a predetermined value, the hardware provided in the endoscope assembly 10 can be effectively used. As the warning unit 129 is provided in the endoscope assembly 10, it is unnecessary to add specific hardware and software to the image receiving unit 20.

The distance can be easily detected by effectively using the hardware provided in the endoscope assembly 10, such as the illumination lens 113, light source unit 114, camera lens 1111, and image sensor 1112.

The endoscope assembly 10 can specify the image receiving unit 20, and sets a channel to be used.

A warning by the warning unit 129 may be an audible beep tone by a buzzer, or may be combined with an LED.

Figure 9:
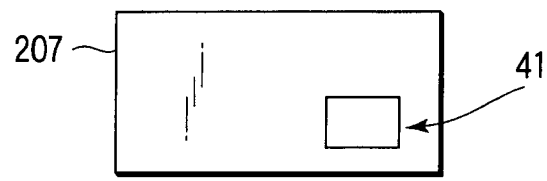
FIG. 9 is a diagram showing a case in which a two-dimensional code is labeled on a housing of an image receiving unit.

A two-dimensional code may be fixed to each image receiving unit 20, and be stuck to the housing 207 of the image receiving unit 20 as a two-dimensional code label 41, as shown in FIG. 9.

Figure 10:
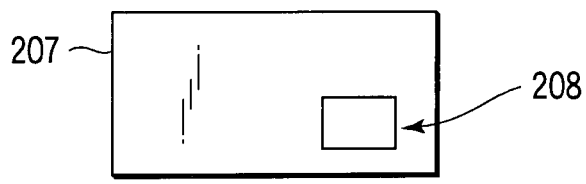
FIG. 10 is a diagram showing a configuration of an image receiving unit in a wireless image acquisition system according to a second embodiment of the invention.

Next, a second embodiment of the invention will be explained. In the first embodiment, the two-dimensional code 40 is displayed on the monitor unit 204. In the second embodiment, as shown in FIG. 10, the display unit 208 dedicated to a two-dimensional code is provided in the housing 207 of the image receiving unit 20.

Figure 11:
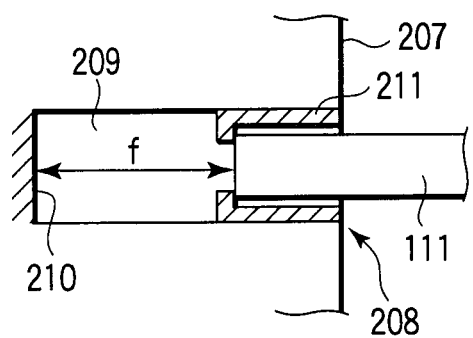
FIG. 11 is a sectional view showing a configuration of a display unit dedicated to a two-dimensional code.

The display unit 208 dedicated to a two-dimensional code comprises a well 209 formed in the housing 207, a display unit 210, and a scope guide 211, as shown in FIG. 11. The display unit 210 is a part to display the two-dimensional code 40 arranged at the bottom of the well 209. The scope guide 211 is removably fit in the well 209. The image acquisition unit 111 of the endoscope assembly 10 is inserted into the scope guide 211. The scope guide 211 is configured to define the distal end position of the image acquisition unit 111 so that the distance from the distal end of the inserted image acquisition unit 111 to the display unit 210 reaches a focused distance f.

Therefore, the endoscope assembly 10 and image receiving unit 20 in the setting mode are completely set simply by inserting the image acquisition unit 111 of the endoscope assembly 10 into the display unit 208 dedicated to a two-dimensional code.

The scope guide 211 of the display unit 208 dedicated to a two-dimensional code can be removed and cleaned by a cleaner to keep cleanness.

As described above, according to the second embodiment, a focal position does not fluctuate with setting conditions when a two-dimensional code is captured. This facilitates the setting.

As the display unit 208 dedicated to a two-dimensional code, the display unit 210 may be arranged on the surface of the housing 207 of the image receiving unit 20, and a projection to insert the scope guide 211 may be provided, rather than providing the display unit 210 to display a two-dimensional code at the bottom of the well 209.

Alternatively, the display unit 210 may be arranged on the surface of the housing 207 of the image receiving unit 20. In this case, a guide cap to be fit to the image acquisition unit 111 of the endoscope assembly 10 is used instead of the scope guide 211. The guide cap may be configured to set the image acquisition unit 111 at a focal position in the state in which the distal end surface of the guide cap contacts the display unit 210.

The invention is explained herein based on the embodiments. The invention is not limited to the embodiments. The invention may be modified or applied in various forms without departing from its spirit or essential characteristics.

For example, the embodiments are explained as an example of a wireless image acquisition system including the endoscope assembly 10 and image receiving unit 20. The invention is also applicable to any wireless image acquisition system, as long as it includes an image acquisition apparatus which transmits acquired image information by radio waves, and an image receiving unit which receives and displays the image information transmitted from the image acquisition apparatus.

Further, in the embodiments, the distance from the endoscope assembly 10, which is an image acquisition apparatus, to the image receiving unit 20 is detected and warned by the image acquisition apparatus. The distance may be detected and warned by emitting light or radio wave from the image receiving unit. In this case, a warning unit may be provided in the image receiving unit 20, and a warning display easily appears in the field of view of a user who watches his (her) hand to bring the image acquisition unit 111 of the image acquisition apparatus, close to the monitor unit 204 of the image receiving unit 20.

Further, in the embodiments, wireless communication setting information is presented as a two-dimensional code in the image receiving unit, and is captured and encoded by the image acquisition apparatus. However, the code is not limited to two-dimensional, and one-dimensional code may be used. Alternatively, text information may be presented by giving the image acquisition apparatus a character recognition function.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A wireless image acquisition system including an image acquisition apparatus configured to wirelessly transmit acquired image information, and an image receiving apparatus configured to wirelessly receive and display the image information transmitted from the image acquisition apparatus, comprising:
a light source unit provided in the image acquisition apparatus and configured to irradiate light;
a warning unit provided in the image acquisition apparatus and configured to give a warning; and
a control unit provided in the image acquisition apparatus and configured to judge whether a reflected light amount of reflected light being obtained from the light irradiated from the light source unit is larger than a predetermined value when making wireless communication setting of the image acquisition apparatus and the image receiving apparatus,
wherein when the reflected light amount is judged to be larger than the predetermined value, the control unit causes the warning unit to give a warning and does not transmit a wireless communication start request signal to the image receiving apparatus, and
when the reflected light amount is judged to be smaller than the predetermined value, the control unit transmits the wireless communication start request signal to the image receiving apparatus and causes the warning unit not to give a warning.

2. The system according to claim 1, wherein
when the reflected light amount is judged to be smaller than the predetermined value, the control unit judges whether focus is achieved by the image acquisition apparatus, and when the focus is achieved, the control unit transmits the wireless communication start request signal to the image receiving apparatus by radio waves based on communication setting information extracted from the image information output from the image acquisition unit.

3. The system according to claim 1, wherein
when the wireless communication setting of the image acquisition apparatus and the image receiving apparatus is completed based on the wireless communication start request signal, the control unit transmits the image information.

4. The system according to claim 2, wherein
when the wireless communication setting of the image acquisition apparatus and the image receiving apparatus is completed based on the wireless communication start request signal, the control unit transmits the image information.

5. The system according to claim 1, further comprising:
a display unit provided in the image receiving apparatus, and configured to display the wireless communication setting information.

6. The system according to claim 5, further comprising:
an image acquisition unit provided in the image acquisition apparatus and configured to acquire an image of the wireless communication setting information displayed on the display unit provided in the image receiving apparatus, the display unit being provided at a bottom of a well formed in a housing of the image receiving apparatus; and
a guide unit provided in the well of the image receiving apparatus and configured to guide the image acquisition unit to a position of focus when the image acquisition unit is inserted to the well to acquire the image of wireless communication setting information.

7. An image acquisition apparatus configured to wirelessly transmit acquired image information to an image receiving unit configured to display the image information wirelessly received, comprising:
a light source unit configured to irradiate light;
a warning unit configured to give a warning;
an image acquisition unit configured to acquire an image and output image information; and
a control unit configured to judge whether a reflected light amount of reflected light being obtained from the light irradiated from the light source unit is larger than a predetermined value when making wireless communication setting of the image acquisition unit and the image receiving apparatus based on the image information output from the image acquisition unit, wherein when the reflected light amount is judged to be larger than the predetermined value, the control unit causes the warning unit to give a warning and does not transmit a wireless communication start request signal to the image receiving apparatus, and when the reflected light amount is judged to be smaller than the predetermined value, the control unit wirelessly transmits the wireless communication start request signal to the image receiving unit based on the wireless communication setting information indicated by the image information output from the image acquisition unit and causes the warning unit not to give a warning.

8. The apparatus according to claim 7, wherein when the reflected light amount is judged to be smaller than the predetermined value, the control unit judges whether focus is achieved by the image acquisition apparatus, and when the focus is achieved, the control unit transmits the wireless communication start request signal to the image receiving unit by radio waves based on communication setting information extracted from the image information output from the image acquisition unit.

9. The apparatus according to claim 7, wherein when the wireless communication setting between of the control unit and the image receiving unit is completed based on the wireless communication start request signal, the control unit transmits the image information output from the image acquisition unit to the image receiving unit.

10. The apparatus according to claim 8, wherein when the wireless communication setting between the control unit and the image receiving unit is completed based on the wireless communication start request signal, the control unit transmits the image information output from the image acquisition unit to the image receiving unit.

* * * * *